US012778616B2

(12) United States Patent
Ries et al.

(10) Patent No.: US 12,778,616 B2
(45) Date of Patent: Nov. 3, 2026

(54) MEDICAL INSTRUMENT SET, MEDICAL DEVICE AND MEDICAL METHOD

(71) Applicant: Joimax GmbH, Karlsruhe (DE)

(72) Inventors: Wolfgang Ries, Linkenheim (DE); Lars Schendzielorz, Linkenheim-Hochstetten (DE)

(73) Assignee: Joimax GmbH, Karlsruhe (DE)

( * ) Notice: Subject to any disclaimer, the term of this patent is extended or adjusted under 35 U.S.C. 154(b) by 302 days.

(21) Appl. No.: 18/542,065

(22) Filed: Dec. 15, 2023

(65) Prior Publication Data

US 2024/0108373 A1 Apr. 4, 2024

Related U.S. Application Data

(63) Continuation of application No. PCT/EP2022/066138, filed on Jun. 14, 2022.

(30) Foreign Application Priority Data

Jun. 15, 2021 (DE) ..................... 10 2021 115 486.3

(51) Int. Cl.
*A61B 17/32* (2006.01)
*A61B 17/00* (2006.01)

(52) U.S. Cl.
CPC .................. *A61B 17/32002* (2013.01); *A61B 2017/00296* (2013.01); *A61B 2017/003* (2013.01);

(Continued)

(58) Field of Classification Search
CPC . A61B 17/16; A61B 17/1615; A61B 17/1671; A61B 17/32002;

(Continued)

(56) References Cited

U.S. PATENT DOCUMENTS 3,613,664 A 10/1971 Willson et al.
5,496,338 A 3/1996 Miyagi et al.

(Continued)

FOREIGN PATENT DOCUMENTS

DE 102018006442 A1 2/2020
EP 0636344 A2 2/1995

(Continued)

OTHER PUBLICATIONS

International Search Report dated Aug. 9, 2022 in corresponding application PCT/EP2022/066138.

*Primary Examiner* — Eduardo C Robert
*Assistant Examiner* — Christina Negrellirodriguez
(74) *Attorney, Agent, or Firm* — Muncy, Geissler, Olds & Lowe, P.C.

(57) ABSTRACT

A medical instrument set having a guide tube and a medical instrument which can be introduced into the guide tube for processing and removing tissue in an intervertebral disc space between two adjacent vertebral bodies. The instrument has a shaft which is rotatable about its extension direction. A set of bristles comprising at least two bristles, with at least one space therebetween, is provided in a distal end region. The space is such that, during rotation of the shaft about its extension direction, processed tissue is movable in an axial direction inside the space. The invention further relates to a medical device and to a medical method.

13 Claims, 14 Drawing Sheets

(52) U.S. Cl.
CPC ............... *A61B 2017/00862* (2013.01); *A61B 2017/00867* (2013.01); *A61B 2017/00982* (2013.01); *A61B 2017/320012* (2013.01); *A61B 2017/320032* (2013.01)

(58) Field of Classification Search
CPC ....... A61B 2017/320032; A61B 2017/320016; A61B 2017/320733; A61B 2017/320012
USPC ............................................... 606/79, 80, 84
See application file for complete search history.

(56) References Cited

U.S. PATENT DOCUMENTS

| | | | | |
|---|---|---|---|---|
| 5,713,369 | A * | 2/1998 | Tao | A61B 10/0291 600/569 |
| 7,722,613 | B2 | 5/2010 | Sutterlin et al. | |
| 11,331,108 | B2 | 5/2022 | Ries et al. | |
| 2003/0191474 | A1 | 10/2003 | Cragg et al. | |
| 2008/0114364 | A1* | 5/2008 | Goldin | A61B 17/1617 606/170 |
| 2008/0208230 | A1 | 8/2008 | Chin et al. | |
| 2010/0057087 | A1* | 3/2010 | Cha | A61B 17/1633 606/80 |
| 2010/0161060 | A1 | 6/2010 | Schaller et al. | |
| 2010/0234848 | A1 | 9/2010 | Sutterlein et al. | |
| 2013/0338533 | A1 | 12/2013 | Olsen | |
| 2014/0058394 | A1* | 2/2014 | Siegal | A61B 17/1671 606/80 |
| 2016/0235418 | A1 | 8/2016 | Mimran | |
| 2016/0287264 | A1 | 10/2016 | Chegini et al. | |
| 2016/0331645 | A1 | 11/2016 | Bagwell et al. | |
| 2017/0100136 | A1* | 4/2017 | Dougherty | A61B 17/32002 |
| 2020/0281579 | A1 | 9/2020 | Zollmann et al. | |

FOREIGN PATENT DOCUMENTS

| | | | |
|---|---|---|---|
| EP | 0763345 | A1 | 3/1997 |
| WO | WO2004024005 | A1 | 3/2004 |
| WO | WO2008103839 | A2 | 8/2008 |
| WO | WO2012125757 | A2 | 9/2012 |
| WO | WO2019081051 | A1 | 5/2019 |

* cited by examiner

MEDICAL INSTRUMENT SET, MEDICAL DEVICE AND MEDICAL METHOD

This nonprovisional application is a continuation of International Application No. PCT/EP2022/066138, which was filed on Jun. 14, 2022, and which claims priority to German Patent Application No. 10 2021 115 486.3, which was filed in Germany on Jun. 15, 2021, and which are both herein incorporated by reference.

BACKGROUND OF THE INVENTION

Field of the Invention

The present invention relates to a medical instrument set having a guide tube and a medical instrument which can be introduced into the guide tube for processing and removing tissue in an intervertebral disc space between two adjacent vertebral bodies. In addition, the invention relates to a medical device comprising the instrument set. Furthermore, the invention relates to a medical method for processing and removing tissue on an intervertebral disc space in an intervertebral disc space.

Description of the Background Art

Medical interventions often provide that human tissue is processed at an intervention site and removed therefrom. For example, in the case of an intervertebral disc degeneration within the scope of a spinal column surgical intervention, tissue is removed in the affected intervertebral disc space, in particular the gelatinous core (nucleus pulposus) between two adjacent vertebral bodies, before an intervertebral cage is introduced into the intervertebral disc space in order to stabilize the vertebral bodies relative to one another. This method is usually referred to as a discectomy, nucleotomy, fragment ectomy or also annulotomy. The (intervertebral disc) tissue is usually processed by means of medical instrument sets having cutting instruments, which are known, for example, from WO 2008/103839 A2.

The known instrument sets with the cutting instruments have the disadvantage that they are designed only for the actual processing task, in particular for severing the tissue. In order to remove the tissue from the intervention site, the cutting instruments must carefully be removed from the intervertebral disc space after they have been used, and then separate removal instruments, specifically provided for this purpose, are introduced into the intervertebral disc space for the intervention site in order to remove the processed tissue. In addition, a full task involving both processing and also removal of the intervertebral disc space is often not possible, in any case only in a very complicated way, which increases the risk of complication of the intervention. The medical interventions are therefore lengthy, complicated, and carry a certain level of risk.

SUMMARY OF THE INVENTION

It is therefore an object of the present invention to provide a medical instrument in which the disadvantages of the prior art are eliminated, and which enables both as complete a processing of the tissue as possible and also its removal from the intervention site. The same applies with respect to the method.

The object of the invention is achieved, in an example, by a medical instrument set, wherein the instrument has a shaft which is rotatable about its extension direction, wherein a set of bristles comprising at least two bristles is provided in a distal end region of the instrument, wherein the set of bristles has at least one intermediate space such that, during rotation of the shaft about its extension direction, processed tissue is movable in a substantially proximal direction within the at least one intermediate space, and wherein the guide tube is designed as a part of a deflection instrument of the instrument set, wherein the deflection instrument has a pivot head which is articulatedly connected to the guide tube and can be pivoted relative to the guide tube, with a distal opening into which the instrument can be introduced at least in portions.

In addition, the object of the invention is achieved by a medical device comprising an instrument set according to the invention and comprising one of the following components: an in particular cannulated working sleeve and/or a working channel of an endoscope, wherein the instrument of the instrument set is axially movable, in particular can be introduced, within the working sleeve and/or within the working channel. Further, the object of the invention is achieved by a medical method comprising the following steps: creating access to the intervention site, introducing an instrument set according to the invention to the intervention site, and rotating the instrument of the instrument set at the intervention site about the extension direction of the instrument in such a way that the tissue of the intervention site is processed and removed.

The invention is based on the basic idea that a gentle processing of the tissue is possible by the bristles of the set of bristles during the rotation of the instrument of the instrument set according to the invention. In the case of interventions in the intervertebral disc space, the processing of the tissue, due to the bristles, is gentle for the bone surfaces of the vertebral bodies arranged adjacently to the intervertebral disc space, especially compared to the known cutting instruments. Since the instrument, in particular its shaft, rotates about its extension direction anyway for processing the tissue, using this rotational movement by means of the intermediate spaces according to the invention can simultaneously move the processed tissue in a proximal direction, i.e., it can be transported away from the site of the intervention. This takes place, for example, similarly to a screw conveyor. In particular, processing of the gelatinous core in the intervertebral disc space is thus easily possible, wherein its processed fragments can be removed particularly quickly from the intervention site. The instrument of the instrument set according to the invention therefore combines two different functionalities for which separate instruments are required in each case. As a result of the pivot head of the deflection instrument, a large-area processing and removal of tissue takes place in a synergetic manner, taking into account the locally prevailing anatomical conditions, in particular of the gelatinous core in the intervertebral disc space. In the sense of the invention, the deflection instrument is designed to stabilize and, in particular, to deflect the instrument according to the invention in a user-defined manner. The same applies to the device according to the invention and to the method according to the invention.

In the sense of the invention, an axial direction denotes a direction which is arranged substantially parallel to the extension direction of the instrument. A radial direction is substantially perpendicular to the axial direction and intersects the extension direction of the shaft. An azimuthal direction is perpendicular to the axial direction and to the radial direction. Proximally denotes a direction pointing toward the user, distally a direction pointing toward the intervention site.

The set of bristles can be arranged helically, for example, in a helical manner about the shaft, wherein the at least one intermediate space can be formed between two windings of the set of bristles. In this way, the intermediate space can also be helical, so that processed tissue is movable in the sense of a screw conveyor when the instrument according to the invention is used. A particularly efficient use of the instrument is thereby possible.

A development of the invention provides that, from the proximal point of view, the set of bristles and/or the at least one intermediate space can be designed to be screw-shaped. As a result, for example, in the event of a rotation of the instrument in the counterclockwise direction, processed material is movable proximally. Preferably, the set of bristles can be arranged in the form of an at least one-start helix, in particular precisely in the form of a one-start helix. The number of bristles can determine the time-based rate of the processed tissue, wherein it should be taken into account that a sufficient intermediate space should still exist between the bristles in order to ensure the removal of the processed tissue and a movement of the bristles when the instrument is introduced.

For the use of the instrument of the instrument set in the intervertebral disc space, the degree of hardness of the bristles can be soft enough that the tissue of the gelatinous core is processed and removed; the end plates of the vertebral bodies delimiting the intervertebral disc space cannot be processed. Alternatively, the degree of hardness of the bristles can be provided to be hard enough that the end plates of the vertebral bodies can be processed. In particular, the degree of hardness of the bristles is selected such that a processing of the spongiosa arranged in the bone interior is possible, wherein preferably no processing of the compacta arranged on the outer side of the bone takes place due to the degree of hardness of the bristles.

In the distal end region, at least two helically arranged wires, twisted together, can be provided, wherein the set of bristles can be connected to the wires in a frictionally engaged and/or form-fitting manner. By using wires that are twisted together, the instrument according to the invention can be produced particularly easily, wherein the set of bristles connected to the wires is reliably held. The set of bristles can be connected to the at least two metal wires in a clamping manner, wherein the metal wires can be designed as clamping wires. In an example of the invention, exactly two wires can be formed which are can be made of metal, preferably of a metal alloy. The wires can have a component made of stainless steel and/or titanium or a stainless steel alloy and/or titanium alloy.

The at least two wires can be connected to the shaft at least indirectly and/or for conjoint rotation, wherein the wires can be arranged in particular distally of the shaft. The bristles can be oriented substantially radially in order to effectively process the tissue. For this purpose, the radial lengths of the bristles of the set of bristles are the same and can be in each case at least twice the diameter of the shaft.

The bristles of the set of bristles can comprise at least one component made of an, for example, rigid or elastic polymer, for example polyamide, and/or of a shape-memory alloy and/or of a resilient metal, such as spring steel or nitinol. The bristles can comprise at least one fiber-reinforced component. The bristles can be manufactured from at least one of these components. The set of bristles and/or the wires can be arranged right-handed from a proximal point of view.

In order to avoid unintentional tissue injuries, in particular distally of the instrument, the distal end face thereof can have an atraumatic tip which can have a round surface at least in portions. In an advantageous development of the invention, the tip can be hemispherical.

In order to prevent unintentional movement of the instrument, in particular in a distal direction, the distal end region thereof can have a radial, in particular conical, preferably cylindrical projection. Due to the radial widening caused by the radial projection, an unintentional movement of the instrument in an axial direction is prevented, in particular unintentional leaving of the intervention site, which overall increases safety. The projection can protrude in the radial direction of the shaft, but the bristles preferably do not. In addition, an outer contour between the distal end face of the instrument and the radial projection can be conical in order to prevent unintentional tissue injuries in this region as well.

In order to protect the at least two wires, the instrument can have at least one sleeve, wherein the at least two wires can be arranged at least in portions within the at least one sleeve. A first sleeve can be formed proximally of the set of bristles and a second sleeve can be formed distally of the set of bristles, wherein the at least two wires can be connected to the sleeves for conjoint rotation. The at least two wires can be connected to the shaft proximally at least indirectly, but preferably for conjoint rotation. The at least two wires can be connected form-fittingly to at least one sleeve, in particular are crimped thereto.

In order to enable a treatment of the tissue at the intervention site over the largest area possible, the distal end region of the instrument can be deflected, preferably can be pivotable, relative to the extension direction of a proximal end region by an angle not equal to 0°, in particular by an angle of 12°, 24° and/or 36° relative to the extension direction of a proximal end region. Preferably, the distal end region can be deflected by an angular range between 0° and 36° relative to the extension direction of the proximal end region. The pivot axis can be arranged substantially perpendicular to the extension direction of the instrument. In this way, tissue that is not arranged along the extension direction of the instrument can also be processed. The use of the instrument set according to the invention is thus adaptable to the anatomy of the intervention site. The distal end region having the set of bristles of the instrument can, for example, be elastically bendable in order to provide a particularly simple possibility of deflection.

In particular, for this purpose, the shaft can be flexible at least in portions, in particular can be manufactured in portions from a shape-memory alloy, for example from a titanium alloy. An example of this is the nickel-titanium alloy known as nitinol. The shaft can in particular be bendable in portions. In the case of the instrument introduced into the deflection instrument, the flexible portion of the shaft can be arranged at the axial height of the pivot head and/or of a joint of the deflection instrument.

At a proximal end region, the instrument can have a driver for transmitting rotational movements to the instrument, so that the necessity for forming actuators is absent. The driver can have, for example, a polygonal or square cross-section in order to enable the simplest possible transmission of torques to the shaft of the instrument. The driver can be connected to the shaft for conjoint rotation and/or can have a greater radial extent than the shaft in an axially centered region.

In a transport position of the instrument, the set of bristles of the instrument can be bendable in the direction of the shaft, in particular in the proximal direction, and/or can be substantially radially oriented, in particular can be re-oriented, in a working position of the instrument. In the sense of the invention, the instrument can assume the transport position during a movement of the instrument to the intervention site and the operating position when using the instrument for processing and removing tissue.

The instrument can be axially movable within the guide tube of the instrument set in order to be able to be reliably moved in this way at the intervention site.

The pivot head can be pivoted relative to the guide tube in a user-defined manner. As a result, in particular in combination with a shaft designed flexibly in portions, the fullest possible processing and clearing of the intervertebral disc space is possible.

The pivot head of the deflection instrument can be arranged at a distal end of the guide tube. In an advantageous development of the invention, the pivot head can be pivotable via an actuatable actuator on a grip of the deflection instrument accessible by the user and via a connecting part, for example a rod assembly or a tab, which is connected to the actuator and the pivot head and is arranged within the guide tube.

The instrument can be rotatable relative to the guide tube about its extension direction, wherein the guide tube can be arranged in particular rigidly. In order to ensure the secure use of the instrument set, the instrument can be axially fixable relative to the guide tube of the deflection instrument. The deflection instrument can have an actuator, which can be connected to the driver of the instrument for conjoint rotation in order to drive the latter in rotation about its extension direction.

The working sleeve of the device according to the invention can be designed, for example, to be cannulated in order to enable simple access to the intervention site, in particular to the intervertebral disc space.

The instrument set according to the invention and/or the device according to the invention for processing and removing tissue, in particular gelatinous core tissue, of an intervertebral disc slot is provided between two adjacent vertebral bodies.

When the instrument of the instrument set according to the invention is introduced, the distal end region thereof can be pivoted relative to the proximal end region in order to move the instrument better at the desired intervention site, the pivot head of the deflection instrument preferably being pivoted. The pivot angle can be between 0° and 36°, wherein in particular pivot angles of 0°, 12°, 24° and/or 36° can be provided. The treatment and/or removal of the tissue at the intervention site can be carried out when the distal end region of the instrument is angled and/or when the pivot head of the deflection instrument of the instrument set according to the invention is angled.

The position and movement of the instrument can be checked by optical inspection, in particular by an endoscope camera, and/or by X-ray inspection, for example by means of a C-arm, so that a correction can optionally be performed as early as possible.

The intervertebral disc space can be accessed from at least one of the following directions: posterior, posterior-lateral, transforaminal, anterior, lateral, craniolateral, transforaminal, and/or intralaminar. The transforaminal access to the intervertebral disc space requires only a small resection of the facet joint and therefore represents a particularly minimally invasive access type to the intervertebral disc space. In addition, the transforaminal access causes only a low level of tissue trauma. The posterior access is suitable, in particular, for the region of the spinal column between the fifth lumbar vertebra L5 and the first sacral vertebra S1 of the sacrum due to the comparatively large interlaminar window present in this region, so that the posterior access is relatively atraumatic. The anterior access enables the introduction of large implants, such as intervertebral cages, for example, but is only recommended in the region of the spinal column caudally of the bifurcation of the aorta to the two large pelvic arteries, the arteria iliaca. The lateral access to the intervertebral disc space represents a particularly simple access possibility and ensures a large support surface for the implant, however, there is a risk of soft tissue trauma.

The method according to the invention can be used, for example, in the context of a treatment of a dysfunctional segment movement of the spinal column, which is also referred to as mechanical instability. The dysfunctional segment movement can be caused, for example, by degenerative changes in the intervertebral disc and/or the movement segment, and by tumors and infections. Secondary instabilities, for the treatment of which the method according to the invention can also be used, are instabilities which have arisen due to other pathologies and/or events, such as tumors or past operations. One example of a dysfunctional segment movement as an application of the method according to the invention is spondylolisthesis (vertebral slip). The method according to the invention is preferably used for preparing an implantation of an intervertebral cage in order to stabilize the spinal column.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
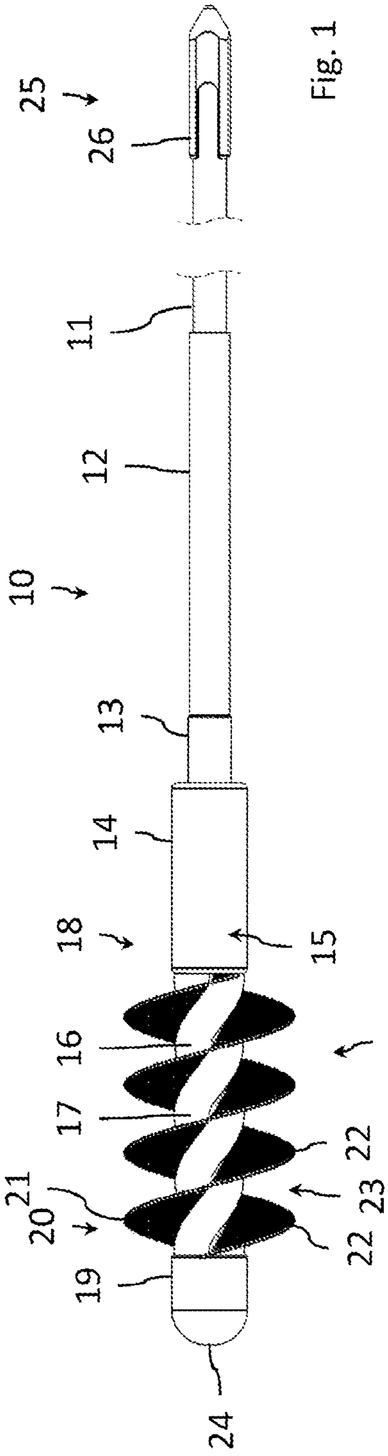
FIG. 1 shows a side view of an instrument of an instrument set according to the invention.

FIG. 1 shows a medical instrument 10 of an instrument set 28 according to an example of the invention in a schematic side view, which instrument has a substantially axial extension direction. The instrument 10 has a coaxially arranged, flexible shaft 11 made of nitinol or stainless steel, wherein the shaft 11 is bendable in particular on a radially widened distal portion 12 about an axis perpendicular to its extension direction, in particular when the instrument 10 is used with a deflection instrument 29 according to the invention described further below.

The instrument 10 has, distally of the flexible shaft 11, a rigid connection part 13 slightly radially widened relative to the shaft 11, which connection part is integrally connected in one piece in the distal direction to a first sleeve 14, and which connects the first sleeve 14 to the shaft 11. The axially oriented first sleeve 14, which is hollow-cylindrical at least in portions, protrudes radially from the connection part 13 and has an inner cavity 15 in which two metal wires 16, 17 are arranged in a distal end region 18 of the instrument 10 and are crimped form-fittingly with the sleeve 14, and thus indirectly with the shaft 11. For reasons of perspective, the cavity 15 and thus also the arrangement of the metal wires 16, 17 within the first sleeve 14 is not shown.

The diameter of the metal wires 16, 17 corresponds in each case approximately to the diameter of the shaft 11. The metal wires 16, 17 are twisted with one another helically such that they form the shape of a double helix that is right-handed from the proximal point of view. The metal wires 16, 17 protrude distally into a second hollow-cylindrical sleeve 19 and are crimped with the latter form-fittingly. The second sleeve 19 has the same diameter as the first proximal sleeve 14, but a smaller axial length.

A set of bristles 20 with radially extending 21 bristles is introduced between the two metal wires 16, 17, wherein the set of bristles 20 is connected to the twisted metal wires 16, 17 in a clamping manner. The set of bristles 20 forms a right-handed screw shape from a proximal point of view, so that, together with the two metal wires 16, 17, a three-start screw shape is present overall. The length of the bristles 21 is at least twice the diameter of a metal wire 16, 17, so that the bristles 21 protrude radially in each case from the two sleeves 14, 19. The bristles 21 are elastic and are made here of an elastic polymer. Alternatively, the bristles 21 can be made of stainless steel, spring steel or nitinol. During a rotation of the instrument 10 about its extension direction, the bristles 21 separate tissue in contact with them. Due to the arrangement of the set of bristles 20 as a right-handed screw, an intermediate space 23 is formed between two adjacent windings 22 of the bristles 21. During a rotation of the instrument 10 about its extension axis, separated tissue is collected in the intermediate spaces 23 and moved in the proximal direction such that the tissue is removed from the intervention site. An accumulation of processed tissue at the intervention site during the processing thereof is thereby avoided. Due to the example of the instrument according to the invention, it is also unnecessary to remove the processed tissue from the intervention site by means of a separate instrument.

The second, distal sleeve 19 has a hemispherical, atraumatic distal surface as the distal end face 24, with which surface undesired tissue injuries are avoided due to its round design when using the instrument 10. In particular, damage to the anulus fibrosus, the fiber ring 57 surrounding the gelatinous core 56, is thereby avoided in the intervertebral disc space 52.

Proximally, the flexible shaft 11 has an end piece 26 with a radially enlarged diameter and a basic shape square in cross section at a proximal end region 25 of the instrument 10. The proximal end piece 26 of the instrument 10 serves as a driver which is designed to transmit torques to the shaft 11 of the instrument 10, so that the driver 26 can be used to drive the instrument 10 in rotational movement about its extension direction, wherein the set of bristles 20 separates surrounding tissue and removes it from the intervention site in the proximal direction via the intermediate spaces 23.

Figure 3:
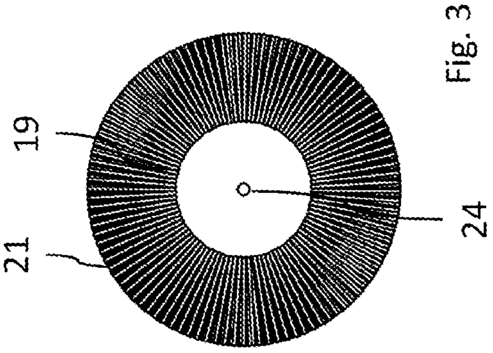
FIG. 3 shows a distal view of the instrument of FIG. 1.
Figure 2:
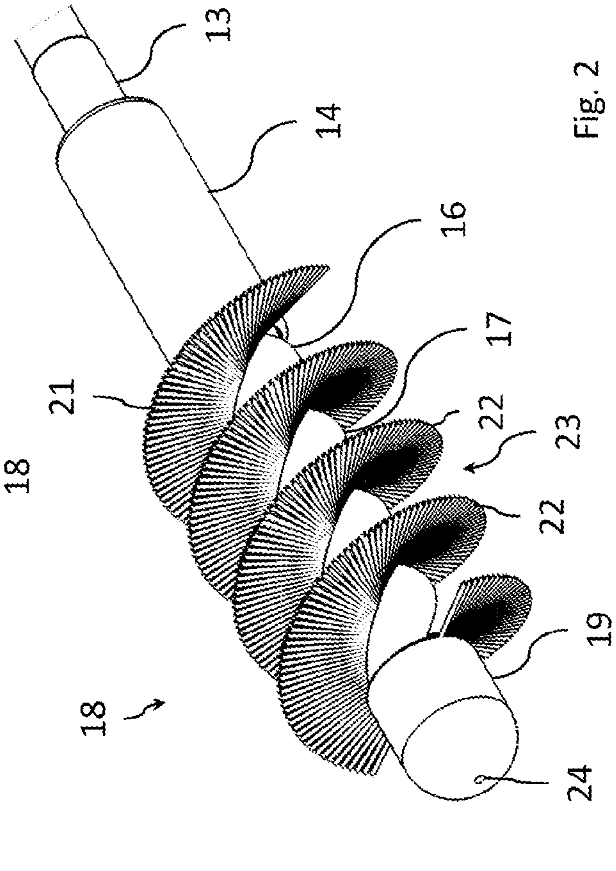
FIG. 2 shows the instrument of FIG. 1 in a perspective view of a distal end region.

FIG. 2 shows the instrument 10 of FIG. 1 in a perspective view in which its distal end region 18 is shown enlarged. FIG. 2 shows in particular the three-start coiled or helical arrangement of the two metal wires 16, 17 and the set of bristles 20, which are right-handed from the proximal point of view, wherein the bristles 21 of the set of bristles 20 each project radially beyond the sleeves 14, 19 and otherwise also the remaining components of the instrument 10. It can be seen from FIG. 2 that the intermediate spaces 23 between the windings 22 of the set of bristles 20 are also arranged in a right-handed helix shape and, compared to the bristles 21, have only half the pitch, i.e., twice the frequency. FIG. 3 shows the instrument 10 of FIG. 1 in a distal view of the atraumatic distal end face 24 and the radially projecting bristles 21 of the set of bristles 20, wherein it can be seen in particular that the radial length of the bristles 21 corresponds approximately to twice the diameter of the distal second sleeve 19.

Figure 4:
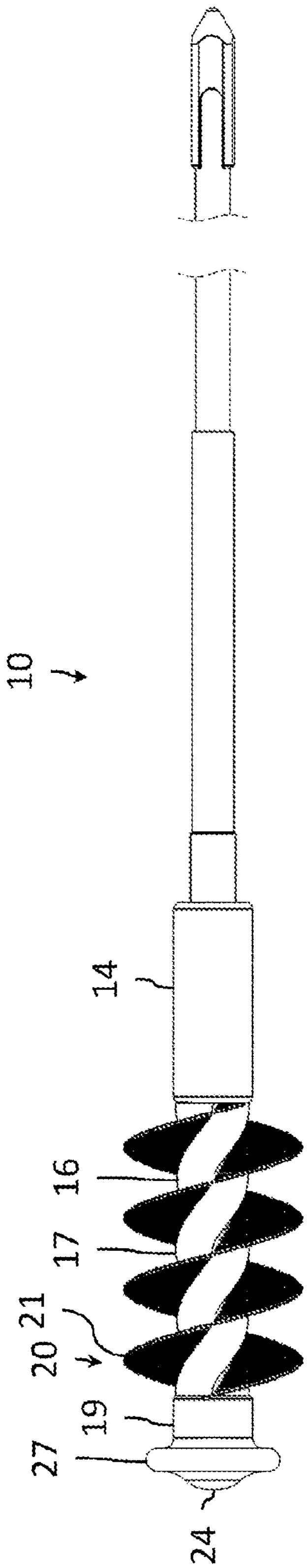
FIG. 4 shows a side view of the instrument in an example.
Figure 6:
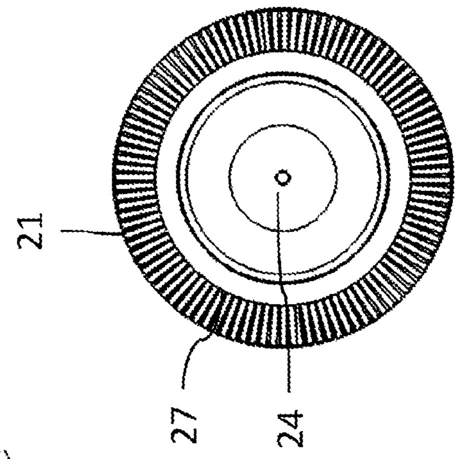
FIG. 6 shows a distal view of the instrument of FIG. 4.
Figure 5:
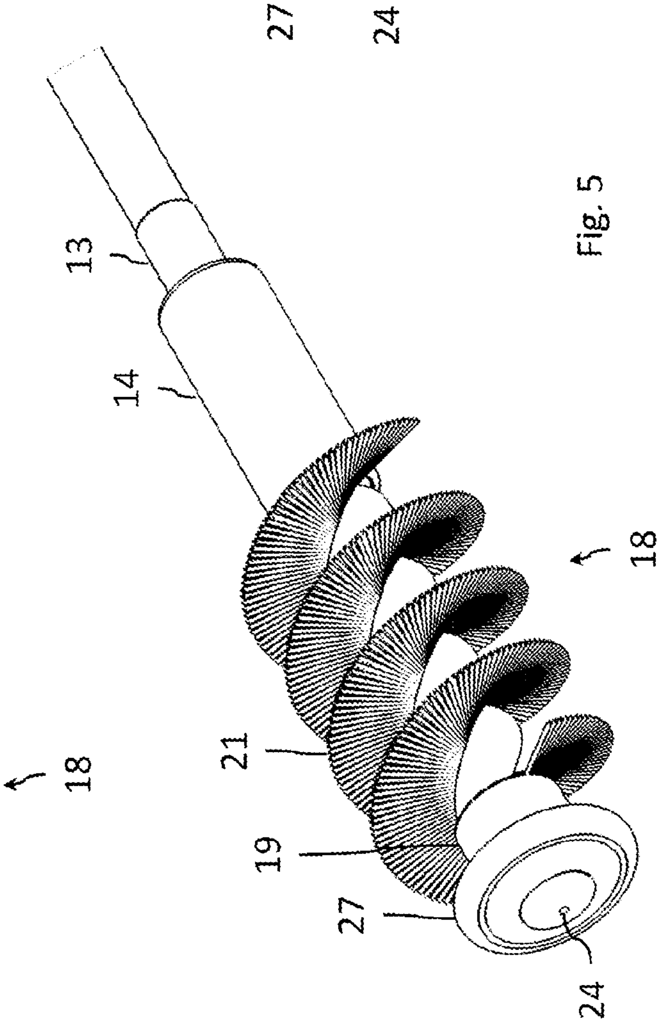
FIG. 5 shows the instrument of FIG. 4 in a perspective view of a distal end region.

FIG. 4 shows an example of the instrument 10 in a side view which differs from the instrument shown in FIG. 1 in particular by the design of the distal end region 18. In FIG. 4, the distal end face 24 does not have a semi-circular design, but rather extends from the distal, round tip 24, continuously and conically to a radial widened projection 27 which is formed integrally with the distal tip 24. Further, in the proximal direction, the transition from the radial projection 27 to the second sleeve 19 is continuous and conical. The radial projection 27 projects radially beyond both the distal tip 24 and the sleeves 14, 19 of the instrument 10, but not the bristles 21 of the set of bristles 20, which is also shown in the side view of FIG. 5 and the distal plan view of FIG. 6. The radial projection 27 serves as a locking mechanism, by means of which, when the instrument 10 is used, an unintentional leaving of the intervention site, for example leaving of the intervertebral disc space 52, is prevented.

Figure 7:
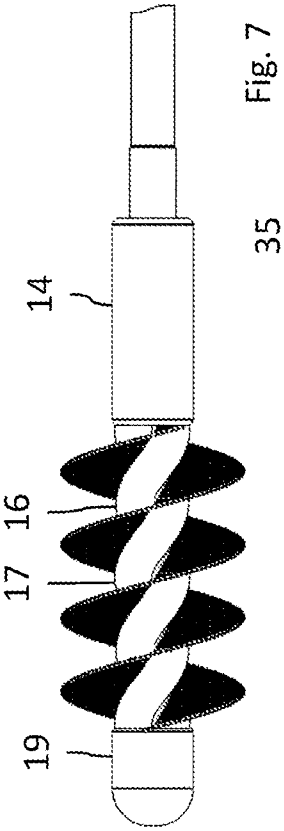
FIG. 7 shows an enlarged view of the distal region of the instrument of FIG. 1.

FIG. 7 shows the instrument of FIG. 1, from which the already described arrangement of the metal wires 16, 17 crimped to the sleeves 14, 19 is apparent.

Figure 8:
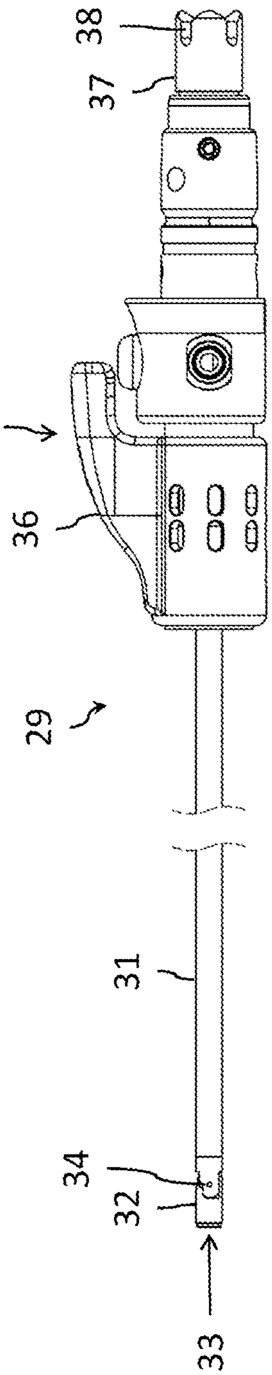
FIG. 8 shows a side view of a deflection instrument of an instrument set according to the invention.

FIG. 8 shows a deflection instrument 29 as part of an instrument set 28 according to the invention in a schematic side view. The deflection instrument 29 has a guide tube 31 which is oriented axially and parallel to the extension direction of the instrument 10, has an axial interior 30, and on which a hollow cylindrical pivot head 32 with a distal opening 33 is pivotably articulated by means of a joint 34. The pivot head 32 is pivotable relative to the rigid guide tube 31 about an axis perpendicular to the extension direction of the guide tube 31, wherein the pivoting movement of the pivot head 32 can be performed in a user-controlled manner. In particular, pivot angles of 0° to 36° are possible. The instrument 10 can be introduced through the distal opening 33 of the pivot head 32 into the deflection instrument 29, which is described further below.

At its proximal end region 35, the deflection instrument 29 has a pivot lever 36 which can be rotated about the extension direction of the guide tube 31 and is connected to the pivot head 32 via a linkage in such a way that the pivot head 32 can be pivoted when the pivot lever 36 is actuated. A connection piece 37 is provided proximally of the pivot lever 36 in order to drive in rotation the shaft 11 of the instrument 10, which shaft is not shown in FIG. 8 and is arranged within the guide tube 31 of the deflection instrument 29. For this purpose, the proximal connection piece 37 of the deflection instrument 29 is provided with slot-shaped recesses 38 distributed over its circumference, in each case axially oriented, into which an actuator 39 shown in FIG. 12 engages form-fittingly. By actuating the actuator 39 on the user side, the proximal connection piece 37 and lastly the shaft 11 of the instrument 10, which shaft is connected to the connection piece for conjoint rotation, can be driven in rotation about its extension direction.

Figure 9:
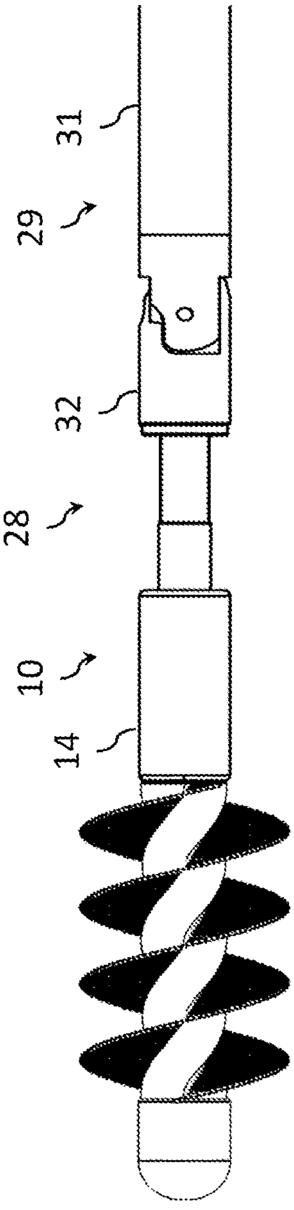
FIG. 9 shows an enlarged side view of an instrument set according to the invention with the deflection instrument of FIG. 8 and the partially introduced instrument of FIG. 1.
Figure 10:
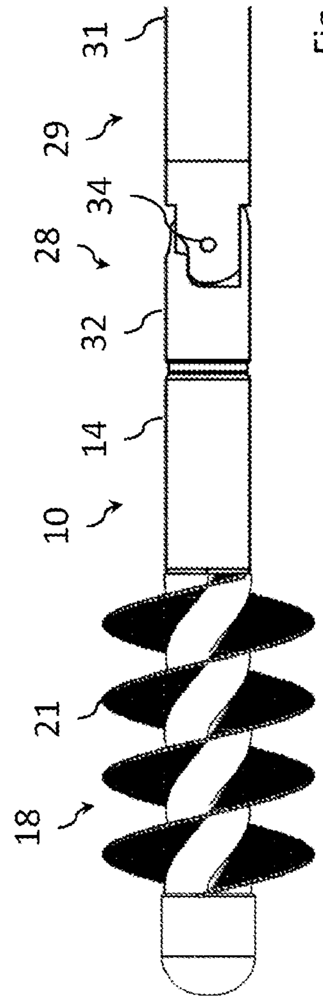
FIG. 10 shows the instrument set of FIG. 9 with the instrument introduced fully.

FIG. 9 shows an instrument set 28 according to the invention comprising the instrument 10 according to FIG. 1 and the deflection instrument 29 according to FIG. 8, wherein the instrument 10, coming from the distal direction, is almost completely introduced into the deflection instrument 29. For this purpose, the instrument 10 is introduced with the proximal end piece 26 into the distal opening 33 of the pivot head 32 and is moved axially further through the interior 30 of the deflection instrument 29, in particular through its guide tube 31, until the proximal first sleeve 14 of the instrument 10 comes into contact with the pivot head 32 and the instrument 10 is introduced into the deflection instrument 29, which is shown in FIG. 10. The diameter of the proximal sleeve 14 of the instrument corresponds to the diameter of the pivot head 32 of the deflection instrument 10, so that, according to FIG. 10, there is a flush transition between the instrument 10 and the deflection instrument 29. The flexible portion of the shaft 11 is located substantially at the axial height of the joint 34. Due to the user-defined deflection of the pivot head 32, the distal end region 18 of the instrument 10, and thus in particular also its set of bristles 20, is also pivotable relative to the proximal end region 25 of the instrument 10, which is described further below.

Figure 11:
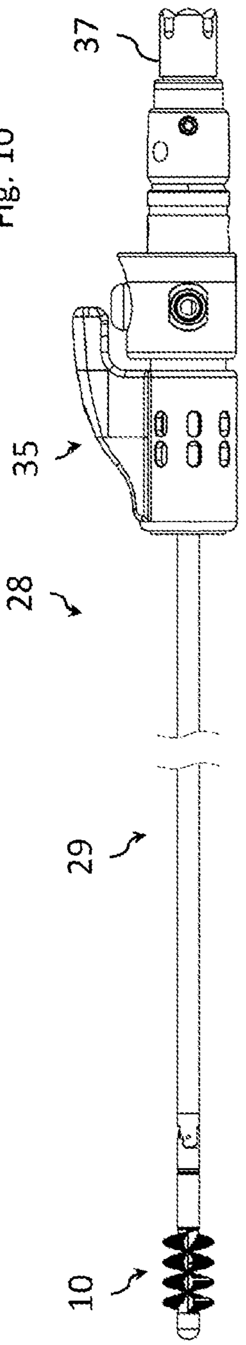
FIG. 11 shows the instrument set of FIG. 10 in a reduced side view.
Figure 12:
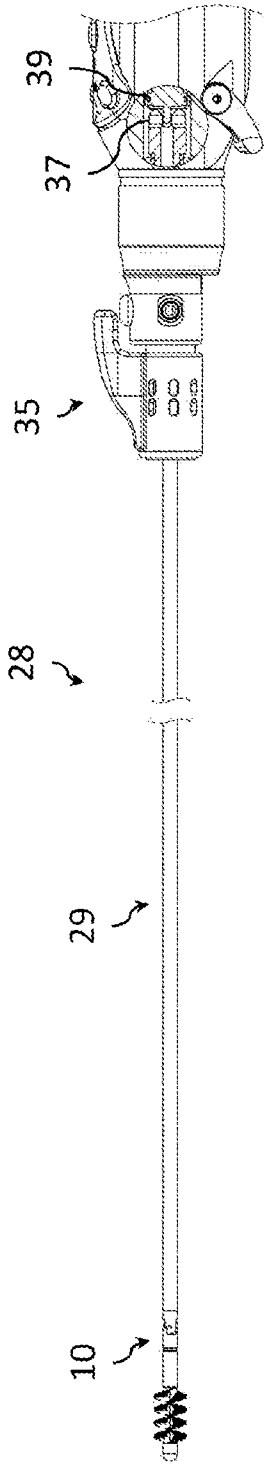
FIG. 12 shows the instrument set of FIG. 11 with an actuator in partial sectional representation.
Figure 13:
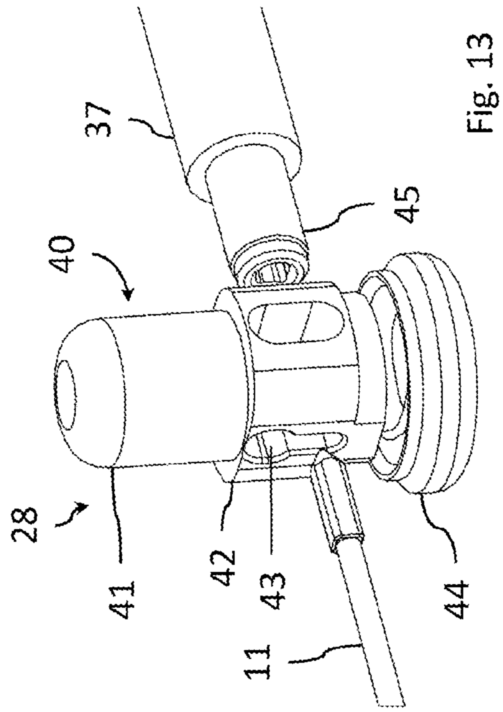
FIGS. 13-17 show perspective views of the proximal region of the instrument with a connector of the deflection instrument.

FIG. 11 shows the instrument set 28 with the instrument 10 according to FIG. 10 introduced into the pivot head 32 in a reduced side view. In FIG. 12, the instrument set of FIG. 11 is provided with the already described proximal actuator 39, which can be seen from the partial sectional representation.

The connection of the instrument 10 to the deflection instrument 29 using a connector 40 of the deflection instrument 29 is described below with reference to FIG. 13 to FIG. 17. According to FIG. 13, the connector 40 has a manually actuatable push-button 41 which is rigidly connected to a central fastening part 42 of the connector 40. The fastening part 42 is substantially cylindrical and has an axial aperture 43, the cross-section of which is designed to be keyhole-shaped: In an upper region, the aperture is wider than in a lower region, so that the cross-section of the aperture tapers downward perpendicular to the axial direction. A mechanical spring 44 is arranged below the push-button 41 and acts on it with a force such that the push-button 41 assumes a rest position shown in FIG. 13 in the non-actuated state. In this position, the shaft 11 of the instrument 10 arranged in the guide tube 31 of the deflection instrument 29 is located at the height of the lower region of the aperture 43, the radial opening of which is smaller than the radial extension of the shaft 11, so that the latter cannot reach through the fastening part 42.

Figure 14:
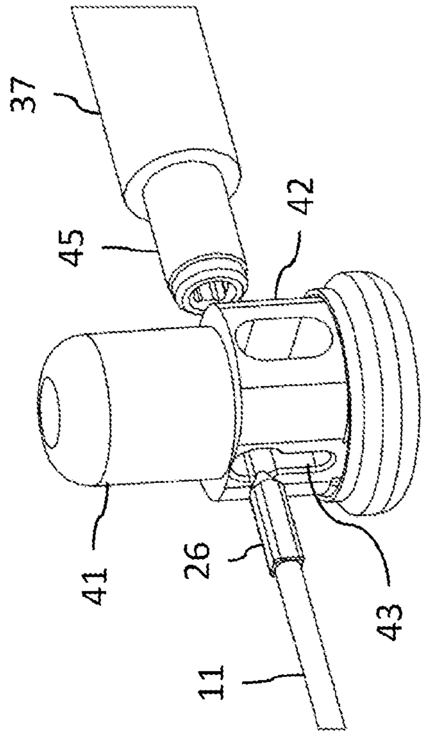
Figure 15:
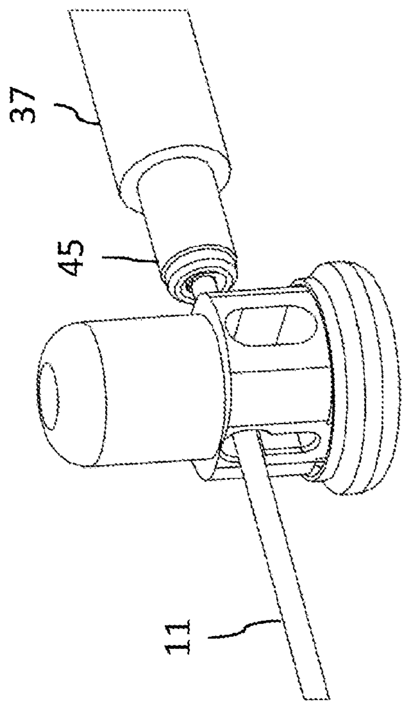
Figure 16:
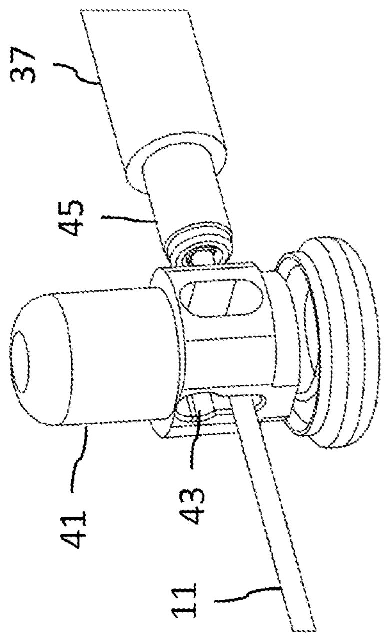
Figure 17:
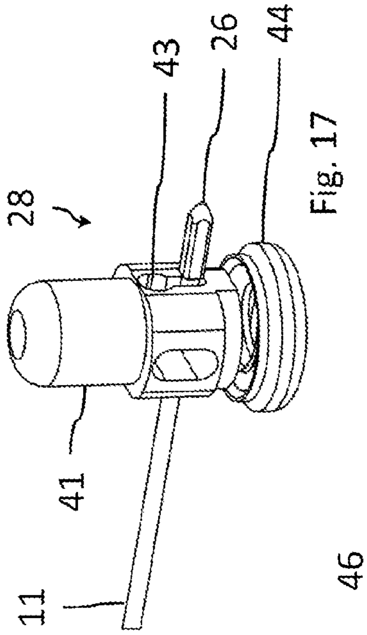

If the push-button 41 is actuated, it assumes the operating position shown in FIG. 14. Accordingly, the upper region of the aperture 43 is now at the height of the shaft 11, so that the latter can pass through the aperture 43, which is shown in FIG. 15. The proximal end piece 26 of the shaft 11 extends completely through the upper region of the aperture 43 and is connected form-fittingly to a distal end piece 45 of the connection piece 37. The proximal end region 25 of the shaft 11 is arranged partially within the aperture 43. If the push-button 41 is released, it assumes the position shown in FIG. 16, so that now the lower region of the aperture 43 is located at the height of the shaft 11, which now no longer can be moved in a distal direction, since the lower region of the aperture 43 has a laterally smaller diameter than the proximal end piece 26 of the shaft 11. The instrument 10 is thus connected to the deflection instrument 29 in an axially form-fitting and captive manner, wherein the lower region of the aperture 43 serves as an undercut. FIG. 17 shows the instrument set 28 of FIG. 13 in this position in a different perspective from which in particular the position of the proximal end piece 26 of the shaft 11 can be seen. During an axial rotation of the distal end piece, the proximal end piece 26 of the instrument 10, and with it the shaft 11, is rotated about the extension direction.

Figure 18:
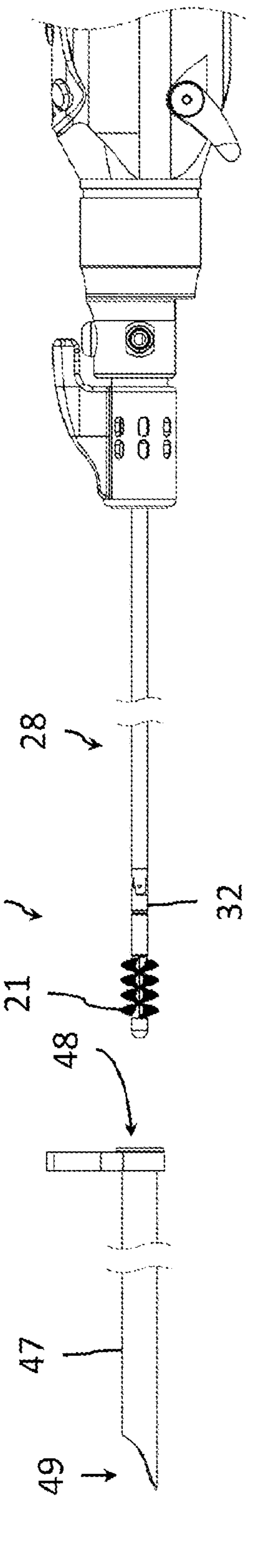
FIGS. 18, 19 show the instrument set of FIG. 11 with a working sleeve.
Figure 19:
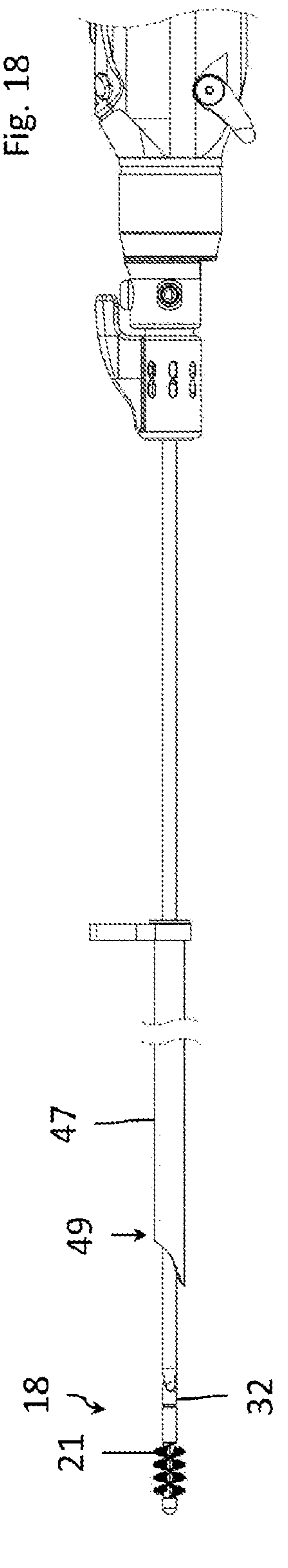

A medical device 46 according to the invention is described below with reference to FIGS. 18 to 19. FIG. 18 shows, in a side view, the medical device 46 according to the invention with a distally arranged and substantially hollow-cylindrical working sleeve 47 and the instrument set 28 of FIG. 12, which is arranged proximally of the working sleeve 47. The working sleeve 47 has an axial lumen 48 and a cannulated distal end face 49 with a conically designed oblique edge. The instrument set 28 is arranged in FIG. 18 proximally of the working sleeve 47 and coaxially thereto.

The diameters of the sleeves 14, 19 of the instrument 10 are in each case smaller than the diameter of the lumen 48, wherein the radial lengths of the bristles 21 are greater than this. The instrument 10 is guided together with the deflection instrument 29 coming from the proximal direction through the lumen 48 of the working sleeve 47, wherein the bristles 21 are bent relative to the proximal direction and to the shaft 11 due to their radial length and their elastic expansion in order to enable the instrument 10 to pass through. In the sense of the invention, the instrument 10 thus assumes a transport position. After the distal end region 18 of the instrument 10 exits from the distal end face 49 of the working sleeve 47, the bristles 21 are re-oriented and are substantially radially oriented, which is shown in FIG. 19. In this respect, the instrument 10 assumes a working position within the meaning of the invention. In this position, the instrument 10 is located, for example, at the intervention site in the intervertebral disc space 52 and can be set in rotation by means of the actuator 39 in order to process tissue of the intervertebral disc space 52. In addition, the pivot head 32 can be pivoted in a user-defined manner in the way already described.

Figure 20:
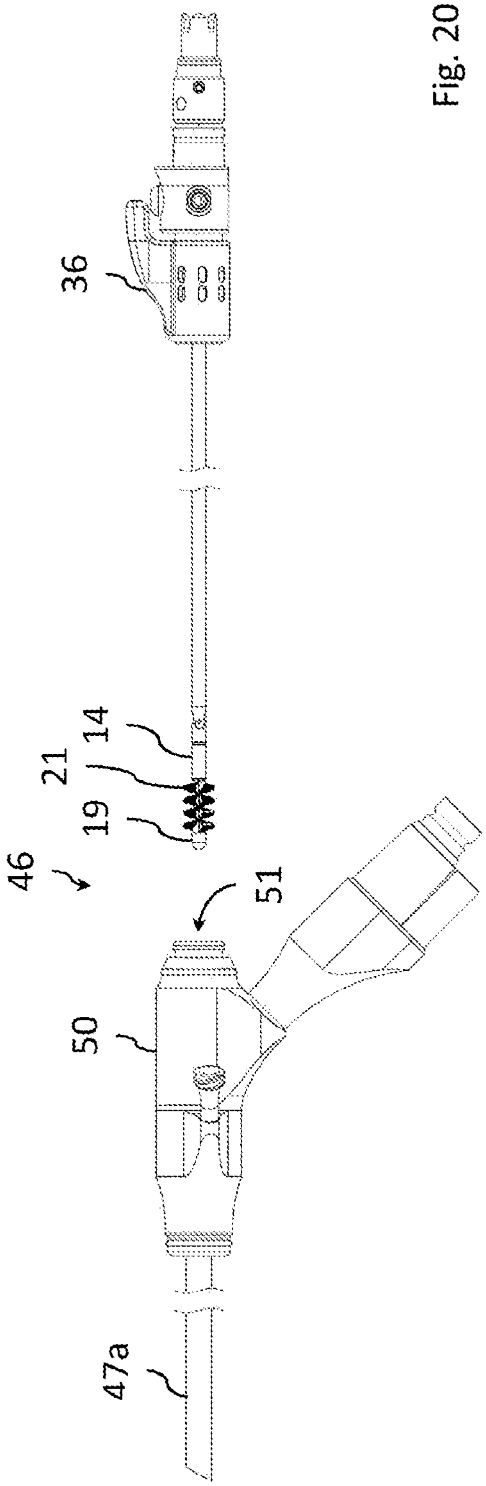
FIGS. 20-22 show the instrument set of FIG. 11 with an endoscope.
Figure 21:
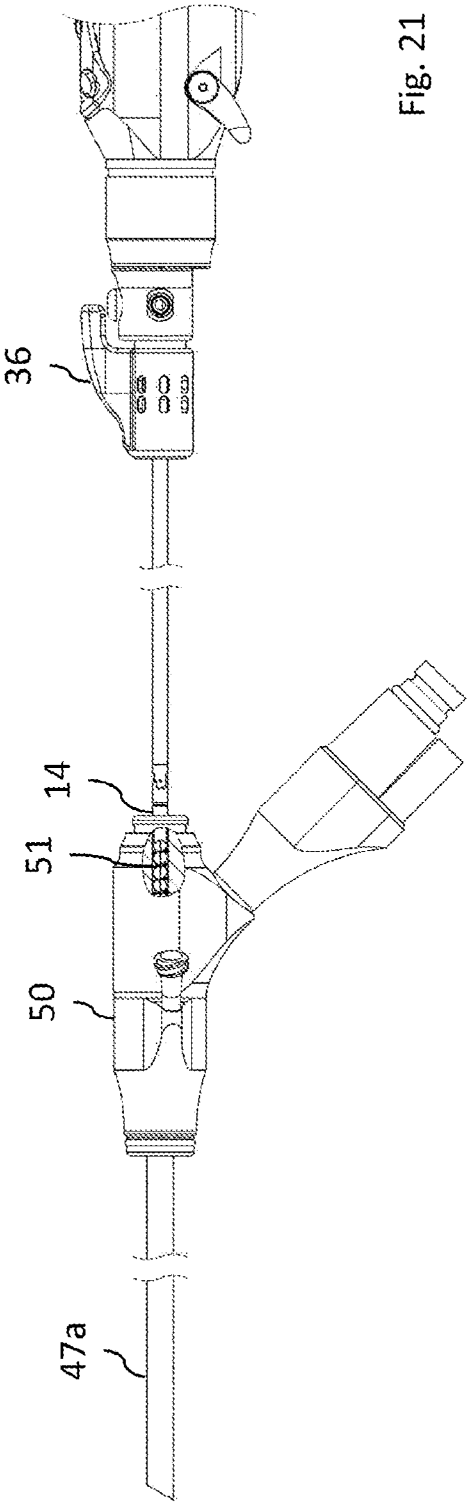
Figure 22:
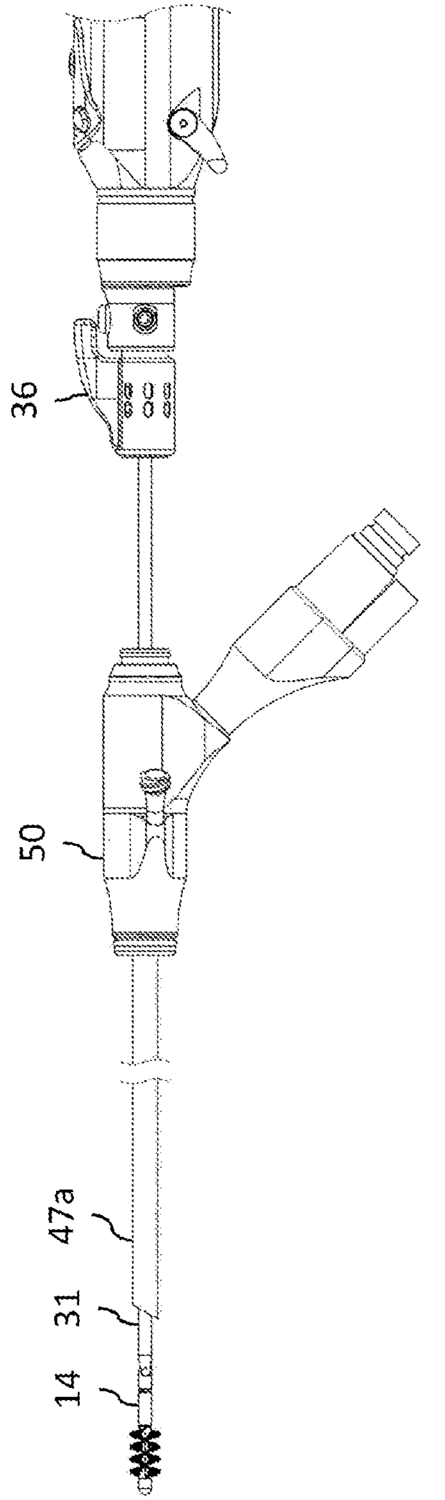

FIGS. 20 to 22 show further examples of the medical device 46 according to the invention with the proximally arranged instrument set 28 and a distally arranged endoscope 50, which has an inner hollow-cylindrical, axial working channel 51 and a distal working sleeve 47*a*. The instrument set 28 is introduced into the working channel 51 of the endoscope 50 coming from the proximal direction, wherein the inner diameter of the working channel 51 is greater than the diameter of the sleeves 14, 19, but smaller than the radial lengths of the bristles 21, so that the latter bend proximally and in the direction of the shaft when the instrument set 28 is introduced, as described above, see FIG. 21. During the distal exit of the instrument set 28 from the working channel 51, the instrument set 28 is located in the working sleeve 47*a*, the inner diameter of which substantially corresponds to the diameter of the working channel 51. When the instrument set 28 is distal from the working sleeve 47*a*, the bristles 21 are re-oriented, which is shown in FIG. 22. In this arrangement, the instrument set 28 can be used as intended for processing and removing the intervertebral disc space 52.

Figure 23:
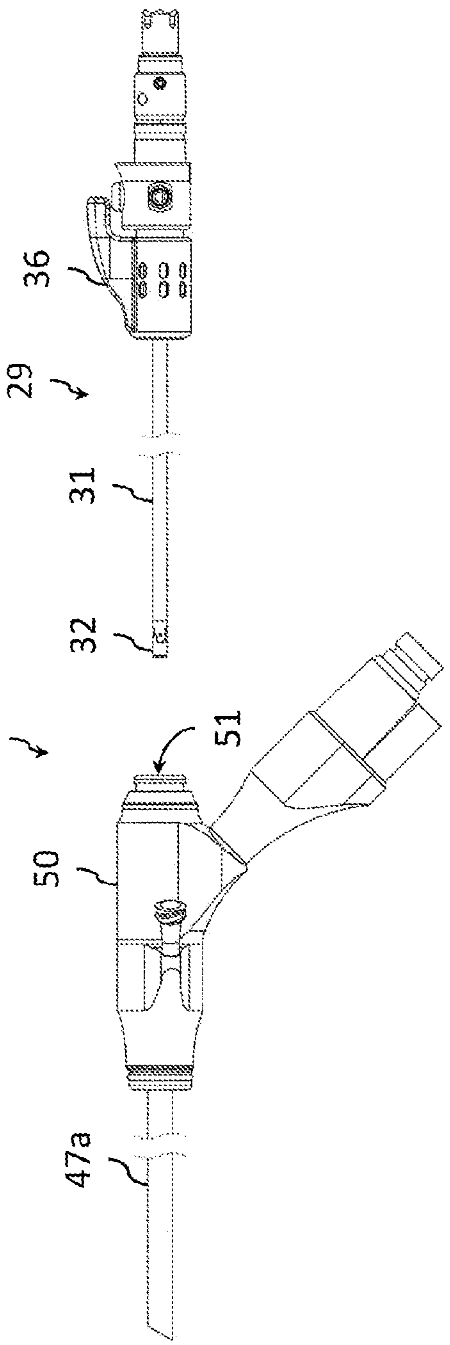
FIGS. 23-25 show the instrument set of FIG. 11 with an endoscope and with a front equipping of the instrument.
Figure 24:
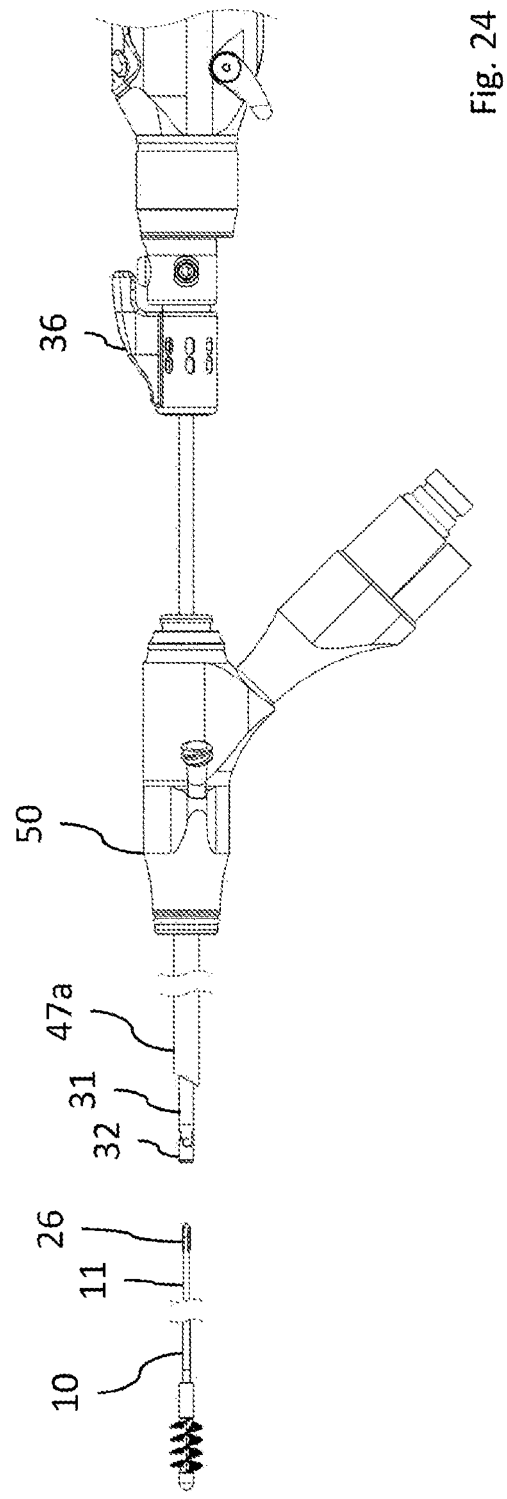
Figure 25:
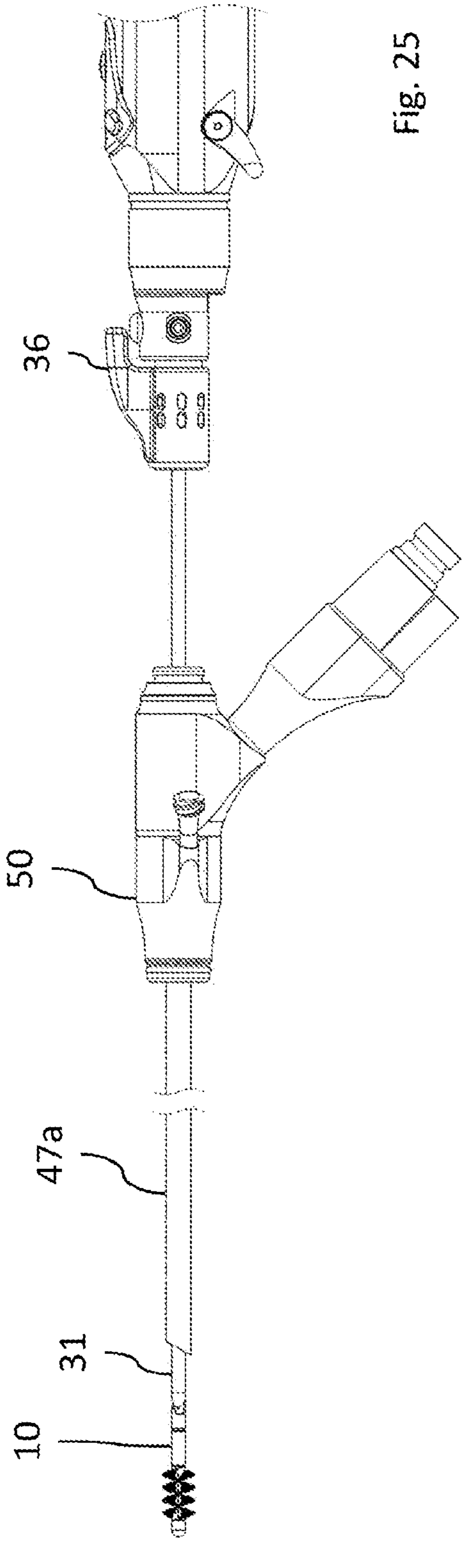

An alternative equipping of the medical device 46 according to FIGS. 20 to 22 is shown in FIGS. 23 to 25. In FIG. 23, only the deflection instrument 29 of the instrument set 28, but not the instrument 10, is arranged proximally of the endoscope 50. As already described, the deflection instrument 28 is, without the instrument 10, moved through the working channel 51 of the endoscope 50 and through its distal working sleeve 47*a*, until the pivot head 32 of the deflection instrument 29 passes completely through the distal working sleeve 47*a*, see FIG. 24. Subsequently, the instrument 10 is introduced from the distal direction into the deflection instrument 29 as already described, i.e., is equipped frontally, see FIG. 25. The device 46 of FIG. 25 thus obtained is substantially identical to the already described device of FIG. 22 after the equipping.

Figure 26:
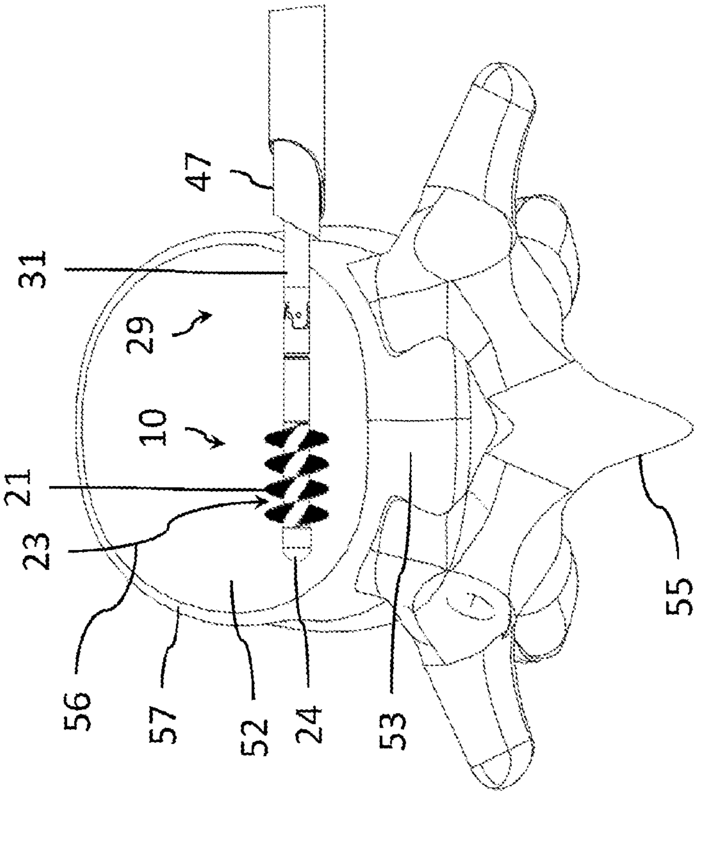

FIG. 26 shows an intervertebral disc space 52 between two adjacent vertebrae 53, 54 and the posterior vertebral extensions 55 associated therewith. The intervertebral disc space 52 has a gelatinous core (nucleus pulposus) 56, which is surrounded by a comparatively hard fiber ring (anulus fibrosus) 57. In FIG. 26, the already described instrument set 28 from the instrument 10 and the deflection instrument 29 penetrates the fiber ring 57, so that in particular the instrument 10 is arranged within the intervertebral disc space 52. The working sleeve 47 surrounding the deflection instrument 29 is located outside the fiber ring 57. The access to the intervertebral disc space 52 takes place from a lateral direction, and is therefore particularly simple and enables a particularly large support surface for an intervertebral cage to be implanted.

In FIG. 26, the pivot head 32 of the deflection instrument 29 is not pivoted and the atraumatic tip 24 of the instrument 10 according to FIG. 1 is arranged at a distance from the fiber ring 57 on the side of the intervertebral disc space 52 opposite the access, wherein unintentional injury to the fiber ring is avoided due to the round configuration of the tip 24. In the position shown in FIG. 26, in the case of a rotation of the instrument 10, which is triggered in a user-defined manner, around its extension direction due to the nature of the bristles 21, the tissue of the gelatinous core 56 surrounding the bristles is separated and, due to the design of the set of bristles 20, is removed from the intervention site through the intermediate spaces 23.

Figure 27:
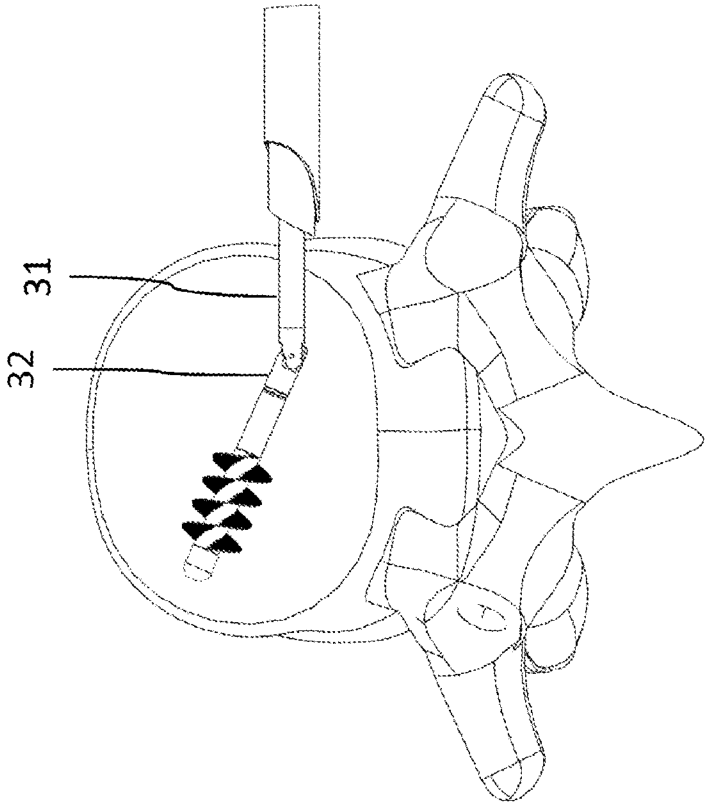
FIGS. 26, 27 show the arrangement of the instrument set of FIG. 11 within an intervertebral disc space in a plan view.

In order to process the intervertebral disc space 52, in particular the tissue of the gelatinous core 56, as completely as possible, the pivot head 32 of the deflection instrument 29 is pivoted relative to the guide tube 31 while maintaining the rotational movement of the instrument 10, which is shown in FIG. 27. The pivot head 32 is pivoted about a substantially vertically oriented axis, so that the pivot head 32 is moved toward the front. As a result, the tissue of the gelatinous core 56 is also processed further and removed from the intervertebral disc space 52. Because the instrument set 28, starting from its position according to FIG. 27, is retracted proximally along its extension direction and the pivot head 32 can additionally be pivoted further, a substantially complete processing of the gelatinous core tissue and thus clearing of the intervertebral disc space 52 is possible. After processing has taken place, the instrument set 28 is completely removed from the intervertebral disc space 52 and retracted proximally through the working sleeve 47.

Figure 28:
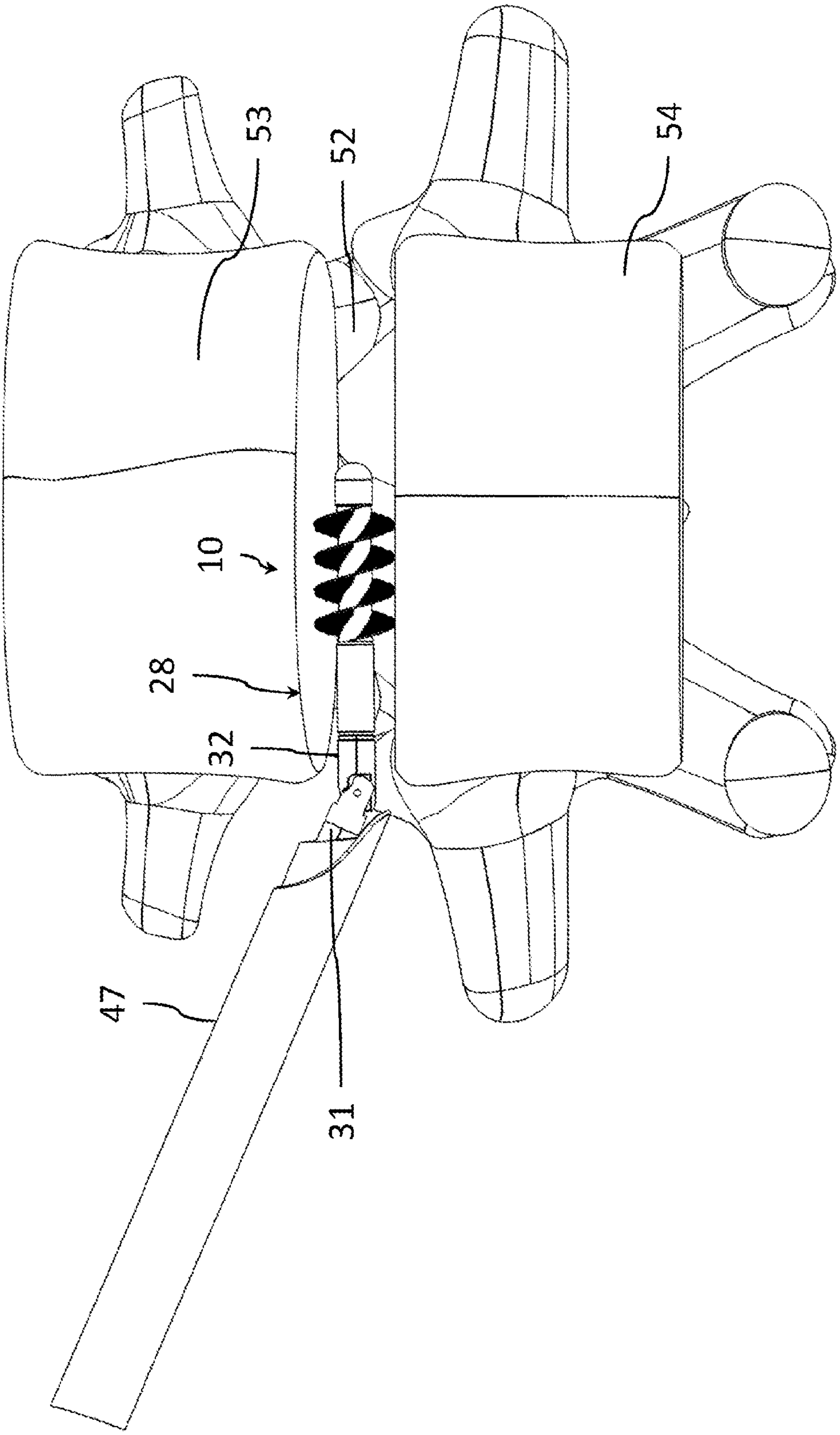
FIG. 28 shows the arrangement of the instrument set of FIG. 26, 27 in a front view.
Figure 30:
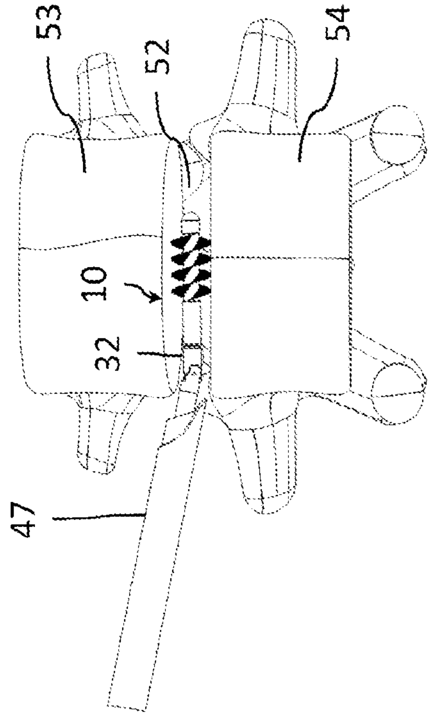
FIGS. 29-31 show the instrument set of FIG. 28 in different pivoting angles.
Figure 31:
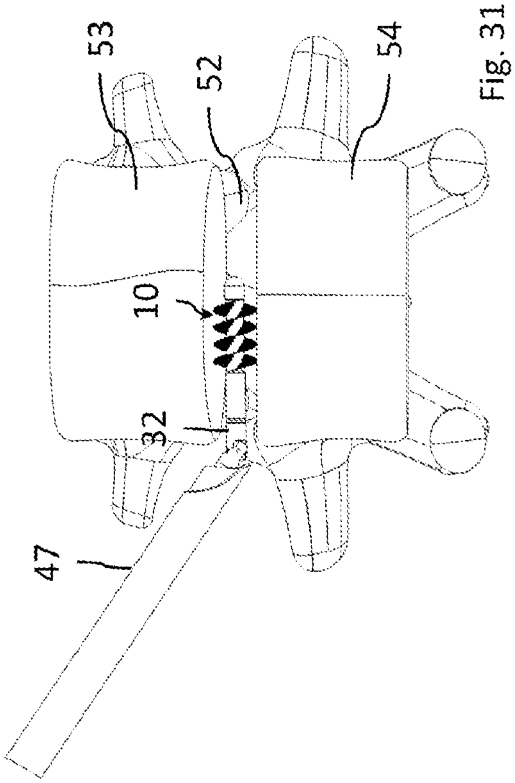
Figure 29:
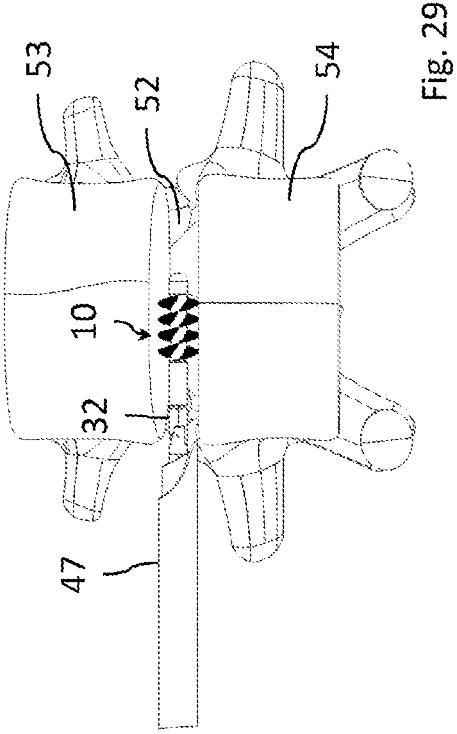

FIG. 28 shows the instrument set 28 arranged in the working sleeve 47 in a posterior view, wherein the instrument set 28 has been rotated through 90° relative to the instrument set of FIG. 27, so that the pivot head 32 is pivotable relative to the guide tube 31 about a sagittal axis of the patient and is pivoted in FIG. 28 at a pivot angle of 24°. The intervertebral disc space 52 is accessed substantially from the craniolateral direction. FIGS. 29 to 31 show the instrument set 28 of FIG. 28 arranged in the working sleeve 47 in the intervertebral disc space 52 with different pivot angles of 0°, 12°, and 36°.

Figure 32:
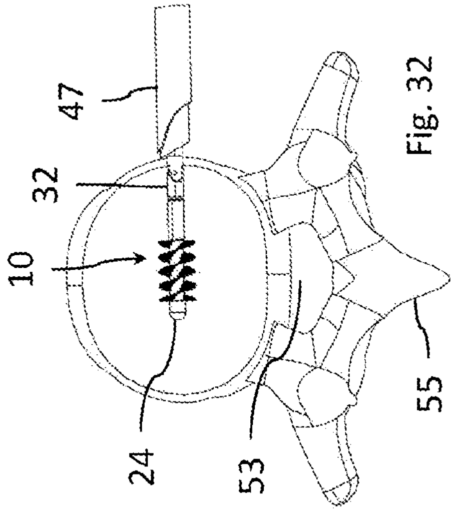
FIGS. 32-36 show access options for the instrument set to the intervertebral disc space.
Figure 33:
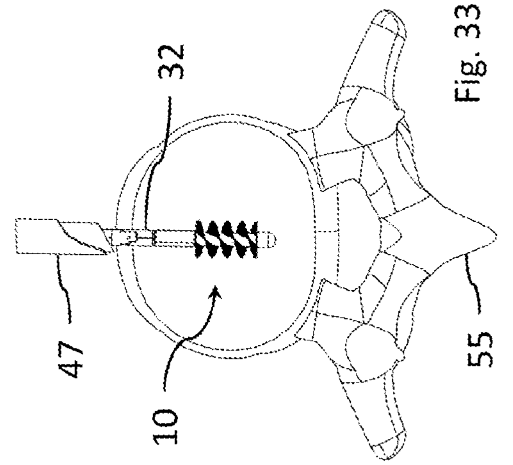
Figure 34:
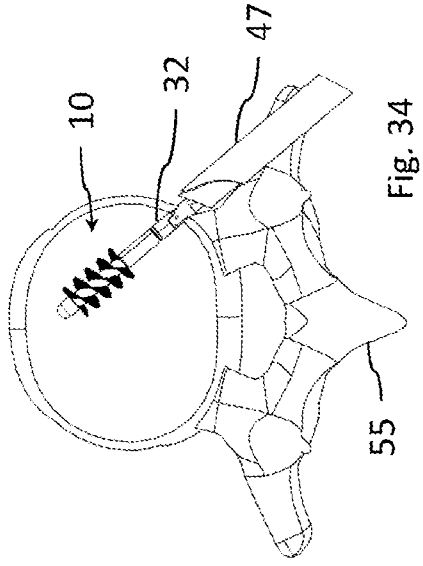
Figure 35:
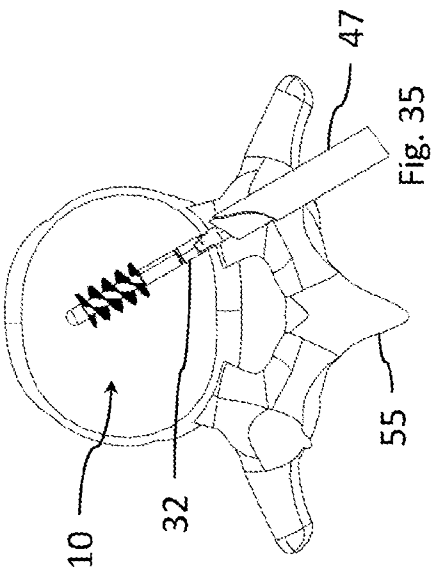
Figure 36:
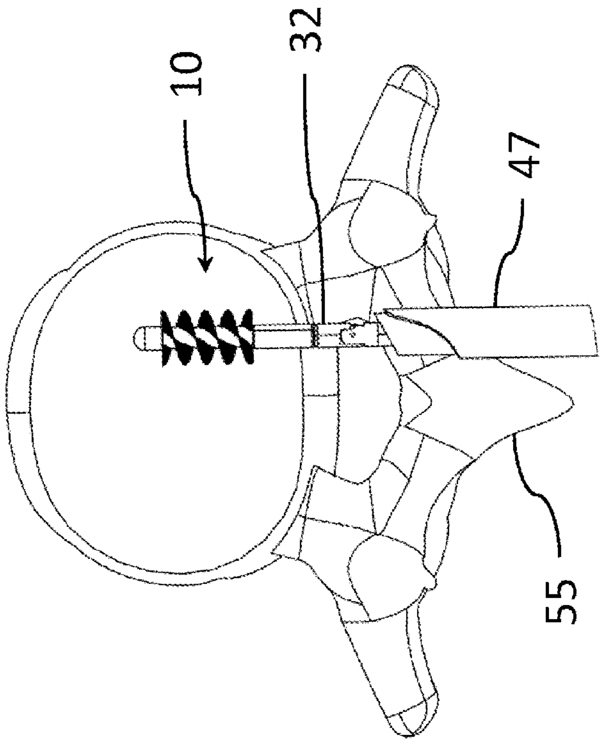

FIGS. 32 to 36 show further access options of the instrument set 28 to the intervertebral disc space 52, wherein the access is also achieved laterally in FIG. 32. In FIG. 33, the access is anterior and enables the implantation of comparatively large implants, in particular intervertebral cages. However, the anterior access according to FIG. 33 is only recommended for regions of the spinal column caudally, i.e., below the bifurcation of the aorta to the two large pelvic arteries, the arteria iliaca. FIG. 34 shows a transforaminal access to the intervertebral disc space 52, which represents a particularly minimally invasive access due to only a small resection of the facet joint. The same applies to the transforaminal access according to FIG. 35, which is slightly pivoted towards the posterior in relation to FIG. 34. Lastly, FIG. 36 shows a posterior access to the intervertebral disc space 52, which is atraumatic in the region of the spinal column between the fifth lumbar vertebra L5 and the first sacral vertebra S1 due to the large interlaminar window present there.

An example of the method according to the invention is explained below with reference to an intervention in the intervertebral disc space 52. First, access to the intervertebral disc space 52 is created by means of known methods, wherein the access is created, for example, on the basis of one of the access options shown in FIGS. 26 to 36. The device 46 shown in FIG. 22 is then moved to the intervertebral disc space 52, wherein the working sleeve 47 does not pass through the fiber ring 57, but already the instrument set 28 with the deflection instrument 29 and the instrument 10. The position and orientation of the instrument 10 are preferably optically controlled, for example by means of an endoscope camera or by means of X-ray inspection, for example by means of a C-arm. Subsequently, the instrument 10 is rotated relative to the working sleeve 47 about its extension direction, as a result of which tissue of the gelatinous core 56 is processed and removed from the intervention site. Subsequently, the pivot head 32 of the deflection instrument 29, while the rotation of the instrument 10 is maintained, is pivoted in a user-defined manner and/or the instrument set 28 is moved further axially until the entire tissue of the gelatinous core 56 has been removed. The device 46 according to the invention is then removed from the intervention site.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A medical instrument set comprising:

a guide tube; and a medical instrument that is adapted to be introduced into the guide tube for processing and removing tissue in an intervertebral disc space between two adjacent vertebral bodies, the medical instrument having a shaft that is rotatable about an extension direction; and a set of bristles comprising at least two bristles are arranged on a distal end region of the instrument, the set of bristles having at least one intermediate space such that, during rotation of the shaft about its extension direction, processed tissue is movable in a substantially proximal direction within the at least one intermediate space, wherein the set of bristles is arranged helically, wherein the at least one intermediate space is formed between two windings of the set of bristles, and wherein the guide tube is a part of a deflection instrument of the instrument set, the deflection instrument having a pivot head that is articulatedly connected to the guide tube and is adapted to be pivoted relative to the guide tube, the guide tube having a distal opening into which the instrument is adapted to be introduced at least in portions.

2. The instrument set according to claim 1, wherein at least two helically arranged wires, twisted together, are provided in the distal end region of the instrument, and wherein the set of bristles are connectable to the wires in a frictionally engaged and/or form-fitting manner.

3. The instrument set according to claim 2, wherein the at least two wires are connected to the shaft for conjoint rotation and are connected at least indirectly.

4. The instrument set according to claim 1, wherein the bristles of the set of bristles are made of an elastic polymer or of a shape-memory alloy or of spring steel or of nitinol.

5. The instrument set according to claim 1, wherein a distal end face of the instrument has an atraumatic or at least partially round surface.

6. The instrument set according to claim 1, wherein the distal end region of the instrument has a radial or conical projection.

7. The instrument set according to claim 1, wherein the distal end region of the instrument is adapted to be deflected or pivoted by an angle not equal to 0° relative to an extension direction of a proximal end region or in a user-defined manner.

8. The instrument set according to claim 1, wherein the shaft of the instrument is flexible at least in portions.

9. The instrument set according to claim 1, wherein, in a transport position of the instrument relative to the shaft, the set of bristles is bendable, and/or wherein the set of bristles are adapted to be oriented substantially radially in a working position of the instrument.

10. The instrument set according to claim 1, wherein the pivot head is pivotable in a user-defined manner relative to the guide tube.

11. The instrument set according to claim 1, wherein the instrument is adapted to be rotated relative to the guide tube about its extension direction or is axially fixed relative to the guide tube.

12. A medical device comprising:

the instrument set according to claim 1; and at least one of the following components:

a cannulated working sleeve; or a working channel of an endoscope, wherein the instrument of the instrument set is axially movable or is adapted to be introduced within the working sleeve or within the working channel.

13. A medical method for processing and removing tissue at an intervention site in an intervertebral disc space between two adjacent vertebral bodies, the method comprising:

creating access to the intervention site;

introducing the medical instrument set according to claim 1 at the intervention site; and rotating the medical instrument of the instrument set at the intervention site about the extension direction of the instrument such that the tissue of the intervention site is processed and removed.

* * * * *